(12) United States Patent
Chen (10) Patent No.: US 7,964,389 B2
(45) Date of Patent: Jun. 21, 2011

(54) QUANTITATIVE SAMPLER OF PATHOGENS IN EXHALED AIR

(75) Inventor: Pei-shih Chen, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 123 days.

(21) Appl. No.: 12/409,298

(22) Filed: Mar. 23, 2009

(65) Prior Publication Data

US 2010/0159575 A1    Jun. 24, 2010

(30) Foreign Application Priority Data

Dec. 24, 2008    (TW) .............................. 97150408 A (51) Int. Cl.
*C12M 3/00* (2006.01)
*G01N 1/22* (2006.01)
*C12Q 1/24* (2006.01)

(52) U.S. Cl. ...... 435/287.2; 422/84; 435/30; 435/287.4; 435/309.1

(58) Field of Classification Search ............... 435/287.2, 435/30, 287.4, 309.1; 422/84
See application file for complete search history.

(56) References Cited

U.S. PATENT DOCUMENTS

| 6,244,096 | B1 * | 6/2001 | Lewis et al. ................. | 73/23.2 |
| 6,485,546 | B2 * | 11/2002 | Fuchs ............................ | 96/135 |
| 7,377,901 | B2 * | 5/2008 | Djupesland et al. .......... | 600/529 |
| 2004/0089302 | A1 * | 5/2004 | Foss ........................ | 128/204.18 |

FOREIGN PATENT DOCUMENTS

JP    2-154802    *    6/1990

OTHER PUBLICATIONS

Burton et al., Ann. Occup. Hyg. 51(2), 143-151 (2006).*
English abstract of Inotsume et al. (JP 2-154802).*

* cited by examiner

*Primary Examiner* — Nathan A Bowers
*Assistant Examiner* — Gautam Prakash
(74) *Attorney, Agent, or Firm* — Kirton & McConkie; Evan R. Witt (57) ABSTRACT

A quantitative sampler of pathogens in exhaled air is provided. The quantitative sampler includes an air inputting pipe for a sampled individual to blow exhaled air; a check valve unit for preventing the exhaled air from reversely flowing; an aerosol filtering unit having an aerosol filtering material for collecting aerosol particles in the exhaled air; and an air flow meter for measuring if total accumulated volume of the exhaled air reaches a predetermined sampling volume defined as a concentration denominator of exhaled pathogens. The quantitative sampler can be used to collect the aerosol particles, and then moves the aerosol filtering material out of the aerosol filtering unit followed by separating genetic substances in the aerosol particles from the aerosol filter, so that a real-time qPCR can be reacted by using the genetic substances for obtaining a quantitative concentration of the exhaled pathogens.

7 Claims, 4 Drawing Sheets

QUANTITATIVE SAMPLER OF PATHOGENS IN EXHALED AIR

FIELD OF THE INVENTION

The present invention relates to a sampler of pathogens, and more particularly to a quantitative sampler of pathogens in exhaled air of sampled individuals.

BACKGROUND OF THE INVENTION

Presently, main spread pathways of various known epidemic diseases (such as influenza virus and etc.) are by air or droplets, so that various related behavior including breathing, coughing, speaking and sneezing may spread pathogens of epidemic diseases. In detail, when patients breath, cough, speak or sneeze, exhaled air of human bodies generally carries a great quantity of aerosols which has a particle diameter ranged between about 5 um and 10 um and may contain various infectious pathogens, so that the pathogens can speedily spread by the aerosols. Thus, it is necessary to develop related samplers and analysis methods, in order to know which kind of pathogen the patients carry in advance before the patients fall ill, or to carry out the purpose of public health and preventive medicine for preventing the epidemic diseases.

Traditionally, many related researches adopt an invasive method of throat swab to enter the throat and the upper palate of the patient for reciprocally scraping the throat and the upper palate several times, in order to collect a sample of throat mucus of the patient. Then, a molecular examination technology is used to analyze if any pathogens exist in the sample of the throat mucus. However, because the throat swab is an invasive means, the common people can not fully accept it, and the scraped portion of the patient may be hurt. Meanwhile, the consistency of the examination result is not high, so that the invasive method of the throat swab is only suitably applied to suspect or infected patients, and difficult to be widely applied to a large-scale plan of public health for preventing the epidemic diseases.

Moreover, see K. P. Fennelly, et al., "Cough-generated Aerosols of *Mycobacterium tuberculosis*: A New Method to Study Infectiousness", Am. J. Respir. Crit. Care Med., Mar. 1, 2004; 169(5): 604-609, which discloses a method to study infectiousness by incubating *Mycobacterium tuberculosis* sampled from cough-generated aerosols of patients, wherein a cough aerosol sampling system is used and connected to a flexible tube. The cough aerosol sampling system is further provided with two impactors therein. Furthermore, a 7H-11 petri dish is used as a sampling medium. In operation, the patient firstly holds the flexible tube in his/her mouth several minutes to sample *Mycobacterium tuberculosis*. Then, the 7H-11 petri dish is used to incubate *Mycobacterium tuberculosis* for obtaining an incubated result to determine if the incubated result is positive or negative. However, the foregoing method only can control the sampling time, but can not precisely control the amount of exhaled air. As a result, the method only can provide a qualitative result, but can not carry out a precise quantitative analysis. In addition, the analysis of *Mycobacterium tuberculosis* by incubating wastes too much time (about 35 days), while the cough-generated aerosols usually contains other pathogens which may affect the determination accuracy of the incubated result.

Besides, see Huynh K N, et al., "A new method for sampling and detection of exhaled respiratory virus aerosols". Clin. Infect. Dis. 2008; 46: 93-95, which discloses a method for sampling and detection of exhaled respiratory virus aerosols, wherein a mask-like device similar to N95 surgical mask is provided with an electret device therein for sampling aerosol particles in exhaled air of a patient. In operation, the patient wears the mask-like device, and coughs or breathes about several minutes. Then, the aerosol particles are separated from the mask-like device, and analyzed by a polymerase chain reaction (PCR) to determine if the aerosol particles contain parainfluenza virus (PIV), influenza virus or other pathogens. However, the foregoing method never detects influenza virus in the mask-like device worn by the patient. In addition, the method only can control the sampling time, and the exhaled air may leak out from edges of the mask-like device. The aerosol particles on the mask-like device may return the respiratory tract of the patient due to breathing behavior. As a result, the method can not precisely control the amount of exhaled air, so that the method still can provide a qualitative result, but can not carry out a precise quantitative analysis.

Furthermore, related researches studied by the inventor of the present invention found that samples of *Mycobacterium tuberculosis* in air of sickrooms may be collected and determined to be positive, but the concentration difference of *Mycobacterium tuberculosis* between these samples may be 10,000 times. Two samples having a concentration difference about 10,000 times have greatly different risks of infection. Thus, if sampling of *Mycobacterium tuberculosis* is operated by a qualitative method, the qualitative result can not provide important information and analysis meaning represented by a concentration of quantitative volume. As a result, it is necessary to develop a quantitative sampler of PATHOGENS in EXHALED air and a quantitative analysis method using the same to solve the problems existing in the traditional technology, as described above.

SUMMARY OF THE INVENTION

A primary object of the present invention is to provide a quantitative sampler of pathogens in exhaled air, which can collect aerosol particles in quantitative exhaled air of sampled individuals by breathing behavior, so as to carry out a quantitative analysis for the purpose of enhancing the sampling convenience and the analysis accuracy, while the quantitative sampler can be applied to the field of public health and preventive medicine for preventing various epidemic diseases.

A secondary object of the present invention is to provide a quantitative sampler of pathogens in exhaled air, which can guide the exhaled air of a sampled individual to pass through an aerosol filtering unit and an air flow meter in turn, so as to collect aerosol particles in a quantitative volume of the exhaled air for the purpose of enhancing the sampling accuracy.

A third object of the present invention is to provide a quantitative sampler of pathogens in exhaled air, wherein aerosol particles collected by the quantitative sampler are quantitatively analyzed by real-time quantitative polymerase chain reaction (also called real-time qPCR hereinafter) to determine the number of genetic substances of a specific pathogen contained in the aerosol particles, so as to calculate the distribution concentration of the pathogen in a quantitative volume for the purpose of enhancing the analysis accuracy and the analysis efficiency.

A fourth object of the present invention is to provide a quantitative sampler of pathogens in exhaled air, which has a check valve unit to prevent exhaled air from returning the respiratory tract of the sampled individual or leaking out, so as to avoid from affecting the calculation of sampling volume of the exhaled air for the purpose of enhancing the quantitative accuracy.

A fifth object of the present invention is to provide a quantitative sampler of pathogens in exhaled air, wherein the air flow meter is further connected to a flow limiting unit, so as to control a predetermined sampling volume of the exhaled air for the purpose of enhancing the quantitative accuracy and the operational convenience.

To achieve the above object, the quantitative sampler of pathogens in exhaled air of a preferred embodiment of the present invention comprises an air inputting pipe, a check valve unit, an aerosol filtering unit and an air flow meter. The air inputting pipe is used for a sampled individual to blow exhaled air. The check valve unit has an air inputting end connected to the air inputting pipe, and an air outputting end. The aerosol filtering unit has a first opening connected to the air outputting end of the check valve unit, a second opening, and an aerosol filtering material disposed therebetween for collecting aerosol particles in the exhaled air. The air flow meter has an air inputting channel connected to the second opening of the aerosol filtering unit, and an air outputting channel, wherein the air flow meter is used to measure if total accumulated volume of the exhaled air reaches a predetermined sampling volume defined as a concentration denominator of exhaled pathogens.

In addition, a preferred embodiment of the present invention provides a quantitative analysis method using the quantitative sampler of pathogens in exhaled air, wherein the method comprises steps of: providing a quantitative sampler including an air inputting pipe, a check valve unit, an aerosol filtering unit and an air flow meter; inputting exhaled air of a sampled individual by the air inputting pipe, preventing the exhaled air from reversely flowing by the check valve unit, collecting aerosol particles in the exhaled air by an aerosol filtering material in the aerosol filtering unit, and measuring if total accumulated volume of the exhaled air reaches a predetermined sampling volume by the air flow meter; moving the aerosol filtering material out of the aerosol filtering unit, and separating genetic substances of exhaled pathogens in the aerosol particles from the aerosol filtering material; and performing a real-time quantitative polymerase chain reaction (real-time qPCR) with the genetic substances for obtaining a quantitative concentration of the pathogens.

In a preferred embodiment of the present invention, the air inputting pipe is further connected to a disposable blow pipe.

In a preferred embodiment of the present invention, the aerosol filtering unit comprises at least two housing which commonly define an inner space for receiving the aerosol filtering material.

In a preferred embodiment of the present invention, the pathogens in the exhaled air are virus, and the aerosol filtering material is a polytetrafluoroethylene (PTFE) filter.

In a preferred embodiment of the present invention, the pathogens in the exhaled air are bacteria or fungi, and the aerosol filtering material is a polycarbonate (PC) filter.

In a preferred embodiment of the present invention, the air flow meter is a dry-type air flow meter.

In a preferred embodiment of the present invention, the genetic substances of the pathogens are deoxyribonucleic acid (DNA) or ribonucleic acid (RNA).

In a preferred embodiment of the present invention, the air outputting channel of the air flow meter is further connected to a flow limiting unit for controlling the sampling volume of the exhaled air.

In a preferred embodiment of the present invention, the flow limiting unit is a flexible bag which has a fixed maximum capacity substantially equal to the predetermined sampling volume of the exhaled air.

In a preferred embodiment of the present invention, the flexible bag has a connection opening which has a sealing film prior to connecting to the air outputting channel.

In a preferred embodiment of the present invention, the flow limiting unit is a hollow cylinder which comprises an air inputting opening, a chamber, a piston and an air outputting opening, wherein the air inputting opening is communicated with the air outputting channel of the air flow meter, the piston is received in the chamber and can be pushed by the exhaled air, and the air inputting opening and the air outputting opening are formed on two different sides of the chamber in relation to the piston.

In a preferred embodiment of the present invention, the piston of the hollow cylinder is connected to a push rod which is extended out of the hollow cylinder for pushing the piston.

In a preferred embodiment of the present invention, the hollow cylinder further comprises an adjusting rod which has a first end extended into the hollow cylinder and a second end extended out of the hollow cylinder for adjusting a maximum motion distance of the piston in the chamber.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
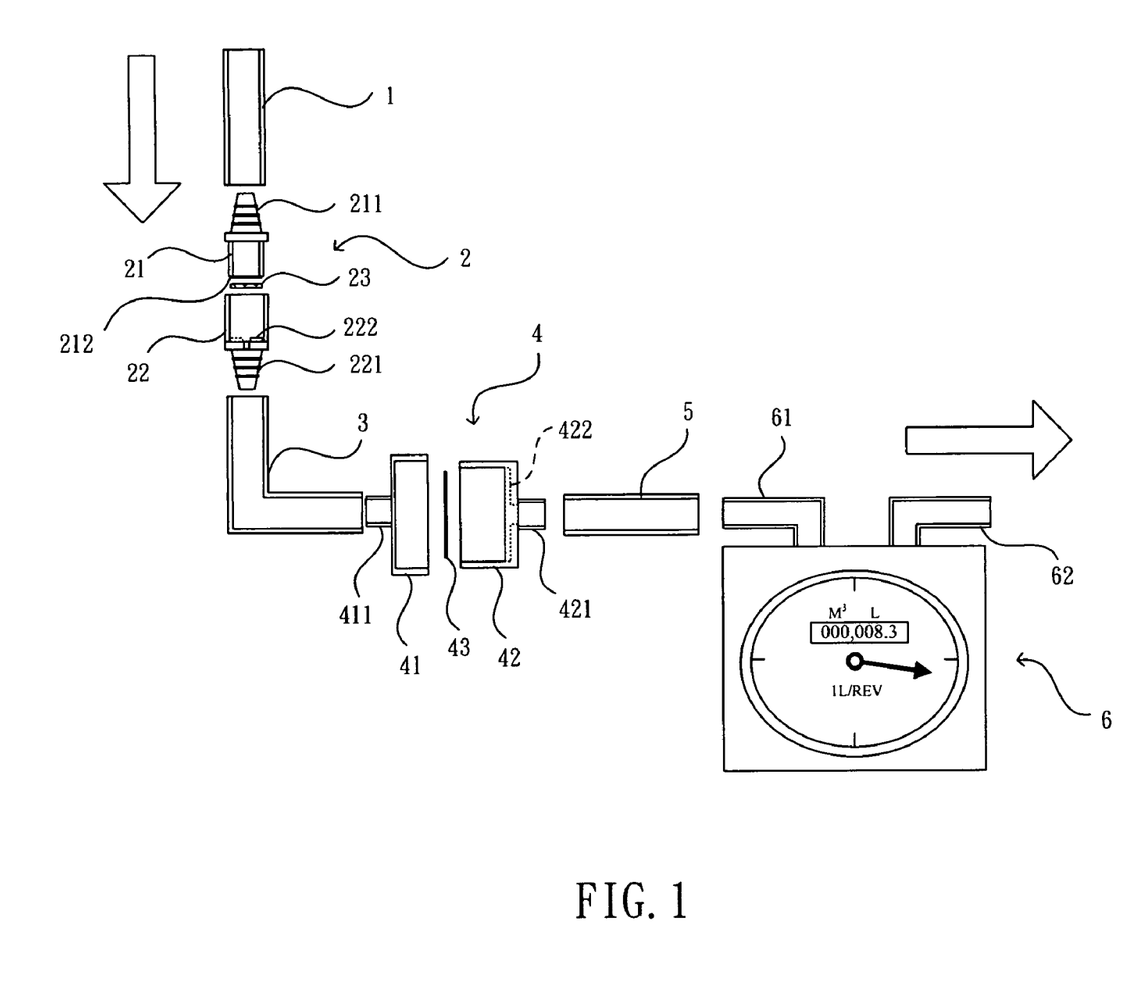
FIG. 1 is a schematic view of a quantitative sampler of pathogens in exhaled air according to a first embodiment of the present invention.

Referring now to FIG. 1, a quantitative sampler of pathogens in exhaled air according to a first embodiment of the present invention is illustrated. As shown, the quantitative sampler comprises an air inputting pipe 1, a check valve unit 2, a first connection pipe 3, an aerosol filtering unit 4, a second connection pipe 5 and an air flow meter 6. The quantitative sampler is applied to a quantitative analysis method of pathogens in exhaled air, so as to speedily collect aerosol particles in quantitative exhaled air of sampled individuals by breathing behavior for carrying out a quantitative analysis. The quantitative sampler and the quantitative analysis method of the present invention can be applied to the field of public health and preventive medicine for preventing various epidemic diseases. For example, the present invention can be applied to collect various pathogens of the respiratory tract including influenza virus, *Mycobacterium tuberculosis* and Enterovirus of the common people or patients by breathing behavior, wherein the pathogens can be virus, bacteria, fungi, and etc. Components of the quantitative sampler and steps of the quantitative analysis method of the present invention will be described more detailed hereinafter.

Referring still to FIG. 1, in the first embodiment of the present invention, the air inputting pipe 1 is preferably selected from a flexible pipe made of silicone, but not limited thereto. The air inputting pipe 1 has a front end (i.e. an upstream end) which is used for a sampled individual to blow exhaled air by his/her mouth for collecting and guiding the exhaled air of the sampled individual. Once the air inputting pipe 1 is used by one of the sampled individual, the air inputting pipe 1 can be detached from the quantitative sampler and replaced by a new air inputting pipe 1 for another sampled individual to blow, so as to lower the disease spread risk during sampling. Furthermore, in a certain condition, the detached air inputting pipe 1 can be recycled after being washed and autoclaved. In one embodiment, the front end of the air inputting pipe 1 can be further connected to a disposable blow pipe (not-shown) for the sampled individual to conveniently blow.

Referring still to FIG. 1, in the first embodiment of the present invention, the check valve unit 2 can be selected from various known check valve. For example, in the first embodiment, the check valve unit 2 has a structure as shown in FIG. 1, which has a first tube 21 having an air inputting end 211, a second tube 22 having an air outputting end 221, and a valve sheet 23, wherein the first tube 21 and the second tube 22 are installed with each other to integrate into one piece. The air inputting end 211 is connected to a rear end (i.e. a downstream end) of the air inputting pipe 1. The valve sheet 23 is preferably selected from a sheet made of elastic material, such as a rubber sheet, which is movably received in an inner space (unlabeled) defined by the first tube 21 and the second tube 22. The first tube 21 is formed with a check flange 212 facing the inner space, while the second tube 22 is formed with a plurality of ribs 222 facing the inner space. When the sampled individual exhales air, the exhaled air of the sampled individual is guided into the air inputting end 211, and the valve sheet 23 is pushed by the exhaled air and abuts against the ribs 222 between which a plurality of gaps (unlabeled) are defined. The gaps between the ribs 222 can allow the exhaled air to pass through the second tube 22, and output from the air outputting end 221. On the other hand, when the sampled individual inhales air, the inhaled behavior of the sampled individual causes a negative air pressure which draws the valve sheet 23 to abut against the check flange 212. Thus, the air pathway of the inner space of the check valve unit 2 is sealed and closed, so as to prevent the air in the inner space from reversely flowing for enhancing the quantitative accuracy of calculating volume.

Referring still to FIG. 1, in the first embodiment of the present invention, the first connection pipe 3 is preferably selected from a flexible pipe made of silicone, but not limited thereto. The first connection pipe 3 is connected the air outputting end 221 of the check valve unit 2 to the aerosol filtering unit 4. The aerosol filtering unit 4 has at least two housing, such as a first housing 41 and a second housing 42, all of which commonly define an inner space (unlabeled). The inner space of the aerosol filtering unit 4 receives an aerosol filter material 43. The first housing 41 is formed with a first opening 411 connected to the air outputting end 221 of the check valve unit 2 via the first connection pipe 3, while the second housing 42 is formed with a second opening 421 connected to the second connection pipe 5. According to types of collected pathogens, the aerosol filter material 43 is preferably selected from a polytetrafluoroethylene (PTFE) filter or a polycarbonate (PC) filter, wherein the PTFE filter is suitably applied to sample various virus including influenza virus and Enterovirus, while the PC filter is suitably applied to sample various bacteria or fungi including *Mycobacterium tuberculosis*. The selection of the aerosol filter material 43 is based on the pore property of material which must be suitably selected to prevent from tightly binding the aerosol particles, to ensure that the aerosol filter material 43 can be advantageous to easily rinse out and separate the genetic substances (such as RNA) of pathogens in the aerosol particles. In addition, the second housing 42 is formed with a plurality of grooves 422 facing the inner space. When the first opening 411 inputs the exhaled air, the aerosol filter material 43 abuts against the surface of the grooves 422. At this time, the exhaled air passes through the pores of the aerosol filter material 43, and outputs from the grooves 422 and the second opening 421. Most of the aerosol particles contained in the exhaled air will be accumulated in the pores of the aerosol filter material 43, so as to finish collecting the aerosol particles contained in the exhaled air.

Referring still to FIG. 1, in the first embodiment of the present invention, the second connection pipe 5 is preferably selected from a flexible pipe made of silicone, but not limited thereto. The second connection pipe 5 is connected the second opening 421 of the aerosol filtering unit 4 to the air flow meter 6. The air flow meter 6 is used to measure if total accumulated volume of the exhaled air reaches a predetermined sampling volume defined as a concentration denominator of exhaled pathogens. The aerosol filtering unit 6 has an air inputting channel 61 connected to the second opening 421 of the aerosol filtering unit 4 via the second connection pipe 5, and an air outputting channel 62 communicated with the atmosphere. The air flow meter 6 is preferably a dry-type air flow meter which can consider the humidity of the exhaled air to exclude the moisture volume of the humid exhaled air for calculate the volume of the dry exhaled air. Meanwhile, the aerosol filtering unit 6 has a meter or a display (unlabeled) to show total accumulated volume of the exhaled air. However, the present invention is not limited to the dry-type air flow meter. In an alternative embodiment, the present invention can use a wet-type air flow meter to calculate the sampling volume. Furthermore, in one embodiment of the present invention, the air outputting channel 62 can be further connected to an additional filter (not-shown) to filter the exhausted air again for preventing the trace pathogens in the exhausted air from polluting the environment. Moreover, the second connection pipe 5 can be connected to the air inputting channel 61 via a dryer (not-shown) for providing dryer material to remove most of moisture in the exhaled air in advance.

Referring now to FIG. 1, the first embodiment of the present invention provides a quantitative analysis method using the quantitative sampler of pathogens in exhaled air, wherein the method comprises steps of: In a first step, providing a quantitative sampler including an air inputting pipe 1, a check valve unit 2, an aerosol filtering unit 4 and an air flow meter 6; In a second step, inputting exhaled air of a sampled individual by the air inputting pipe 1, preventing the exhaled air from reversely flowing by the check valve unit 2, collecting aerosol particles in the exhaled air by an aerosol filtering material 43 in the aerosol filtering unit 4, and measuring if total accumulated volume of the exhaled air reaches a predetermined sampling volume by the air flow meter 6; In a third step, moving the aerosol filtering material 43 out of the aerosol filtering unit 4, and separating genetic substances of exhaled pathogens in the aerosol particles from the aerosol filtering material 43; In a fourth step, performing a real-time quantitative polymerase chain reaction (real-time qPCR) with the genetic substances for obtaining a quantitative concentration of the pathogens.

Referring back to FIG. 1, in the first embodiment of the present invention, the first step of the quantitative analysis method using the quantitative sampler of pathogens in exhaled air is to provide a quantitative sampler including an air inputting pipe 1, a check valve unit 2, an aerosol filtering unit 4 and an air flow meter 6. In the step, the detailed structure of the quantitative sampler has been described hereinbefore, wherein the aerosol filtering material 43 of the aerosol filtering unit 4 is selected from a polytetrafluoroethylene (PTFE) filter (outer diameter 37 mm; pore diameter 0.02 um) if the collected pathogens in the exhaled air are influenza virus, and the air flow meter 6 is a dry-type air flow meter.

Referring still to FIG. 1, in the first embodiment of the present invention, the second step of the quantitative analysis method using the quantitative sampler of pathogens in exhaled air is to input exhaled air of a sampled individual by the air inputting pipe 1, prevent the exhaled air from reversely flowing by the check valve unit 2, collect aerosol particles in the exhaled air by an aerosol filtering material 43 in the aerosol filtering unit 4, and measure if total accumulated volume of the exhaled air reaches a predetermined sampling volume by the air flow meter 6. In the step, the sampled individuals of the present invention are exemplified by children of a certain kindergarten, wherein three classes of children with different year olds (3-6 year olds) are sampled several individuals at random. For example, six individuals are sampled from each of the three classes to carry out the sampling experiments of influenza virus of exhaled air, wherein total number of sampled individuals is 18. The sampling frequency is several times per week (such as 3 times per week), and the sampling duration is several days (such as 15 days, total sampling times are 7), so that several exhaled air samples are collected (such as 126 samples). When the children is tested, the children (i.e. the sampled individual) hold the front end of the air inputting pipe 1 (or the disposable blow pipe) by their mouths, and the children are guided to inhale by their noses and exhale by their mouth as far as possible. Thus, the children can smoothly blow the exhaled air into the air inputting pipe 1 under normal breathing frequencies. During the children exhale, the check valve unit 2 can prevent the exhaled air from reversely flowing, so as to enhance the quantitative accuracy of the exhaled air. Meanwhile, aerosol particles contained in the exhaled air will be filtered and accumulated in the pores of the aerosol filter material 43 in the aerosol filtering unit 4. When the meter of display of the air flow meter 6 shows that total accumulated volume of the exhaled air of the children reaches a predetermined sampling volume (such as 10 liters), the children are asked to stop exhaling air, so as to finish collecting quantitative exhaled air. In the present invention, the predetermined sampling volume is used to be defined as a concentration denominator of pathogens in exhaled air in the following step for calculating the concentration of exhaled pathogens.

Referring still to FIG. 1, in the first embodiment of the present invention, the third step of the quantitative analysis method using the quantitative sampler of pathogens in exhaled air is to move the aerosol filtering material 43 out of the aerosol filtering unit 4, and separate genetic substances of exhaled pathogens in the aerosol particles from the aerosol filtering material 43. In the step, if the collected pathogens are influenza virus, the genetic substances of the pathogens are ribonucleic acid (RNA). Alternatively, if the collected pathogens are bacteria, fungi or some type of virus, the genetic substances of the pathogens are deoxyribonucleic acid (DNA). After finishing the second step, opening the at least two housings 41, 42 of the aerosol filtering unit 4 to move the aerosol filtering material 43 out of the aerosol filtering unit 4. Then, the air inputting pipe 1, the check valve unit 2 and the aerosol filtering unit 4 are detached from the air flow meter 6, and change a new set of the air inputting pipe 1, the check valve unit 2 and the aerosol filtering unit 4 for another sampled individual to use. Furthermore, in a certain condition, the detached components can be recycled after being washed and autoclaved. After moving out the aerosol filtering material 43, the aerosol filtering material 43 is wrapped and sealed by an aluminum foil (not-shown), and stored under 4° C. After the aerosol filtering material 43 is transported to a laboratory, an isolation of genetic substances (such as virus RNA) within 3 days. In the embodiment, the present invention uses QIAamp Viral RNA Mini Kit manufactured by QIAGEN to isolate the virus RNA, but not limited thereto. The isolated virus RNA can be stored under $-20°$ C. to $-70°$ C.

Referring still to FIG. 1, in the first embodiment of the present invention, the fourth step of the quantitative analysis method using the quantitative sampler of pathogens in exhaled air is to perform a real-time qPCR with the genetic substances for obtaining a quantitative concentration of the pathogens. In the step, the present invention firstly performs a reverse transcription polymerase chain reaction (RT-PCR) with the virus RNA as a template for obtaining a complementary DNA (cDNA). Then, the cDNA is used to perform a real-time qPCR to duplicate and increase the number of genetic substances (i.e. DNA) for a quantitative concentration analysis. In the embodiment, the present invention uses Taq-Man One-Step RT-PCR Master Mix Reagents Kit manufactured by ABI to perform the RT-PCR, and uses ABI PRISM 7500 Sequence Detection System manufactured by ABI to perform the real-time qPCR. During the two PCRs, known primers of influenza A or B virus and fluorescent-labeled probes are used. When performing the real-time qPCR, the virus RNA and related reagents are placed into centrifuge tubes, and the centrifuge tubes are placed into the foregoing machine to perform the real-time qPCR, wherein a reverse transcription reaction is firstly performed about 30 minutes under 48° C., and then a polymerase activation is performed about 10 minutes under 95° C., followed by performing 40 times of amplification cycles about 15 seconds under 95° C. and 1 minutes under 60° C., so as to duplicate and increase the number of DNA. To keep the experimental accuracy, a positive control group (added with a quantitative standard cDNA) and a negative control group (only added with diethyl pyrocarbonate (DEPC) water) are simultaneously performed for comparing with an experimental group. Finally, the foregoing machine finishes the real-time qPCR, and measures the fluorescent intensity of the fluorescent-labeled probes carried by the duplicated DNA to obtain a quantitative reference value of DNA.

Figure 2:
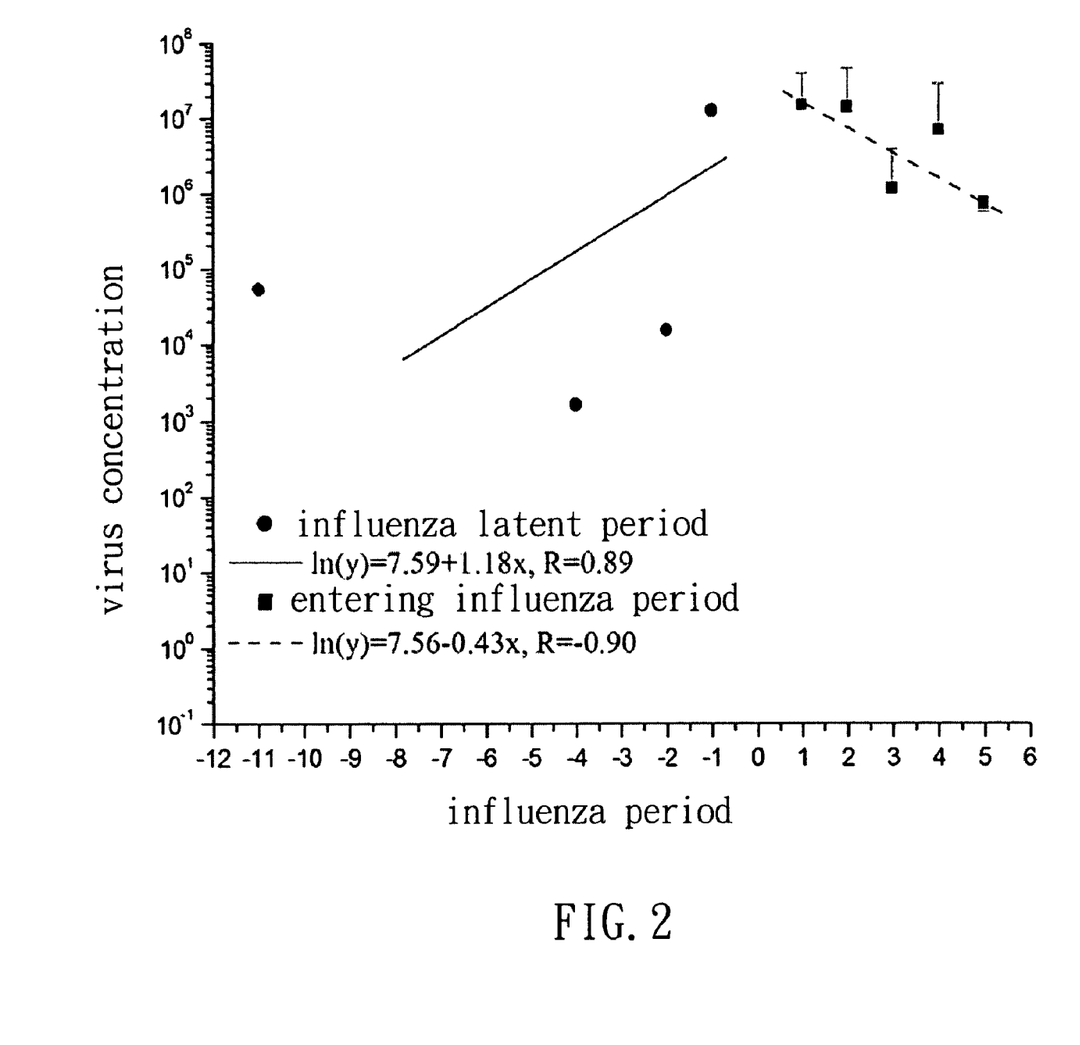
FIG. 2 is a statistic graph of influenza virus concentration in exhaled air of sampled individuals and influenza period of the sampled individuals according to the first embodiment of the present invention.

Referring now to FIG. 2, a statistic graph of influenza virus concentration in exhaled air of sampled individuals and influenza period of the sampled individuals according to the first embodiment of the present invention is illustrated, wherein X axis represents the day before/after an influenza fall-ill day (day 0), and Y axis represents the logarithm reference concentration converted from the virus concentration. Among 18 sampled children of 3-6 years old, 16 individuals of them suffered from influenza during the sampling period. As shown in FIG. 2, during the sampling period, the children who were sampled on days −4, −2 and −1 before the influenza fall-ill day, i.e. the children who were in influenza latent period, can be detected the virus from their exhaled air. Especially, when the day in influenza latent period is gradually close to the influenza fall-ill day, the virus concentration of the children will increase. Furthermore, among the children who were sampled on days 1~5 after the influenza fall-ill day, the children of days 1 and 2 has a maximum virus concentration of exhaled air, while the children on day 4 of influenza period still has a positive virus detection. The children on day 5 have an apparent lowered virus concentration. In addition, among the children of 6 years old, the children of days 1~3 can be detected with the influenza virus in their exhaled air, but the virus concentration of the children after day 3 will be lower than a predetermined minimum detection valve. However, among the two children groups of 4-5 years old, the children on day 4 after the influenza fall-ill day, who almost recover, can be detected with the influenza virus in their exhaled air, wherein the virus concentration is gradually lowered. The foregoing analysis result shows that the younger children have weaker immunity, while the virus may stay in the body thereof for a longer time. Therefore, in the present invention, the quantitative sampler of pathogens in exhaled air and the quantitative analysis method using the same can be used to gather statistics about relationships of virus concentration of exhaled air, ages and latent days in advance, so as to calculate related reference information tables. Thus, when a general investigation of public health about a specific pathogen is performed, the related reference information tables can be used to predict which latent stage the sampled individuals are in.

As described above, in comparison with traditional sampler of pathogens and analysis method which can not carry out a precisely quantitative analysis, the quantitative sampler of pathogens in exhaled air and the quantitative analysis method using the same of the present invention can collect aerosol particles in quantitative exhaled air of sampled individuals by breathing behavior, so as to carry out a quantitative analysis. Thus, the quantitative sampler and the quantitative analysis method of the present invention is advantageous to enhance the sampling convenience and the analysis accuracy, and can be applied to the field of public health and preventive medicine for preventing various epidemic diseases. Furthermore, the quantitative sampler of the present invention can guide the exhaled air of a sampled individual to pass through an aerosol filtering unit 4 and the air flow meter 6 in turn, so as to collect aerosol particles in a quantitative volume of the exhaled air for the purpose of enhancing the sampling accuracy. Moreover, the aerosol particles collected by the quantitative sampler are quantitatively analyzed by real-time qPCR to determine the number of genetic substances of a specific pathogen contained in the aerosol particles, so as to calculate the distribution concentration of the pathogen in a quantitative volume for the purpose of enhancing the analysis accuracy and the analysis efficiency.

Figure 3:
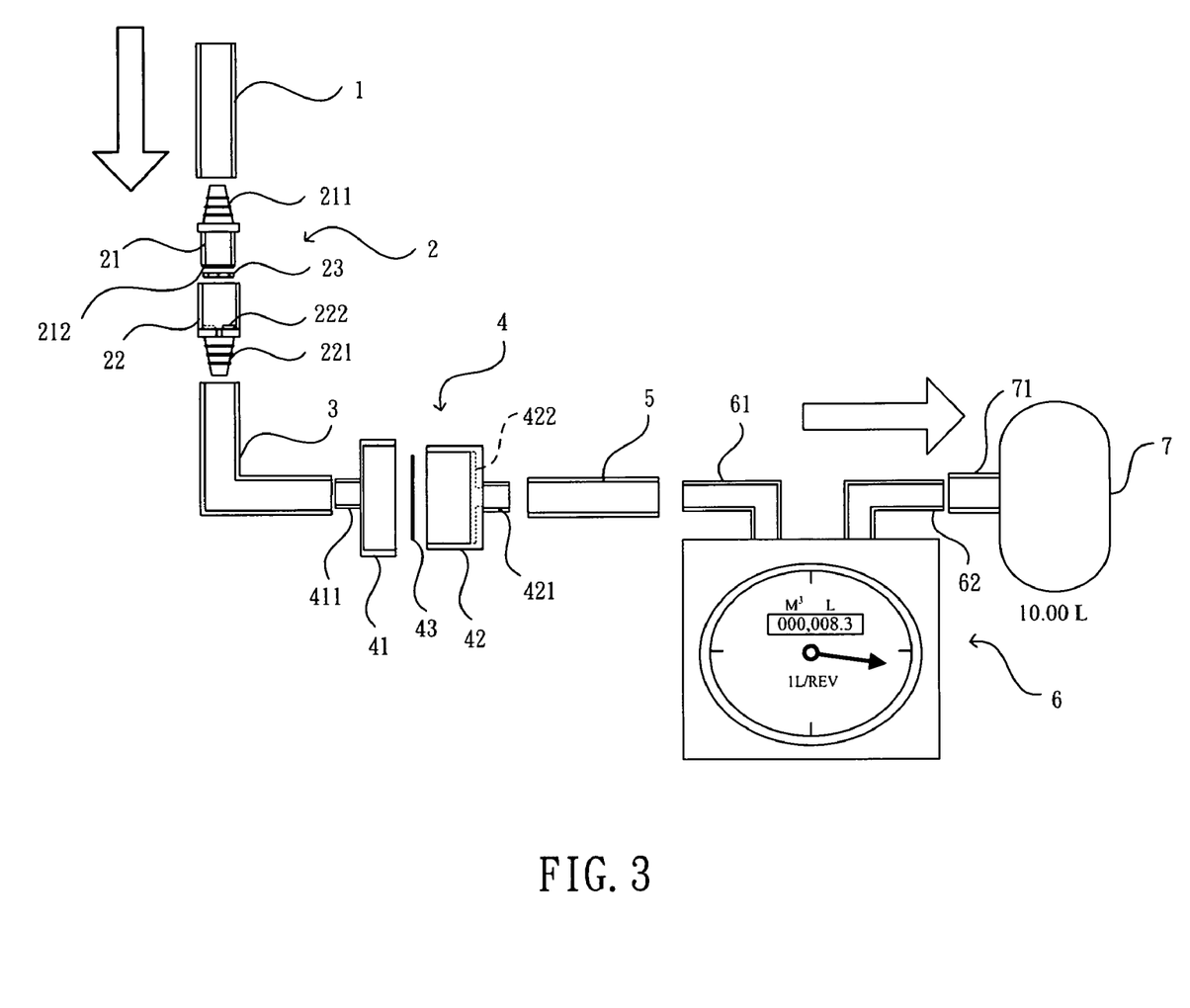
FIG. 3 is a schematic view of a quantitative sampler of pathogens in exhaled air according to a second embodiment of the present invention.

Referring now to FIG. 3, a quantitative sampler of pathogens in exhaled air according to a second embodiment of the present invention is illustrated and similar to the first embodiment, so that the second embodiment uses similar numerals and can be applied to the same quantitative analysis method. As shown, the quantitative sampler of pathogens in exhaled air according to the second embodiment further comprises a flow limiting unit 7 which is connected to the air outputting channel 62 of the air flow meter 6 for controlling a predetermined sampling volume of the exhaled air. In the second embodiment, the flow limiting unit 7 is a flexible bag (such as a plastic bag) which has a fixed maximum capacity substantially equal to the predetermined sampling volume (such as 10 liters) of the exhaled air. The flow limiting unit 7 has a connection opening 71 which is connected to the air outputting channel 62. Before the flow limiting unit 7 is in use, the flexible bag is in a compressed status and an inner space thereof is in a vacuum status without air. The connection opening 71 preferably has a sealing film (not-shown) to ensure the vacuum status. When the air outputting channel 62 is inserted into the connection opening 71, the sealing film will be punctured, so that the flow limiting unit 7 can be communicated with the air flow meter 6.

When the quantitative sampler of the second embodiment of the present invention is used by a sampled individual, the exhaled air of the sampled individual passes through the air flow meter 6 and gradually flows into the flow limiting unit 7, so as to expand the flow limiting unit 7. When total accumulated volume of the exhaled air is equal to the fixed maximum capacity (such as 10 liters) of the flow limiting unit 7, the flow limiting unit 7 can not be further expanded. Thus, the sampled individual will be reminded that the quantitative exhaling operation is finished, so as to enhance the quantitative accuracy and the operational convenience. After the flow limiting unit 7 is used, the flow limiting unit 7 can be detached from the air flow meter 6 and replaced by a new flow limiting unit 7 for another sampled individual to use. In addition, if wanting to change the setting of the predetermined sampling volume of the exhaled air, the present invention can select to use another flow limiting unit 7 with different capacity specification for providing a different fixed maximum capacity.

Figure 4:
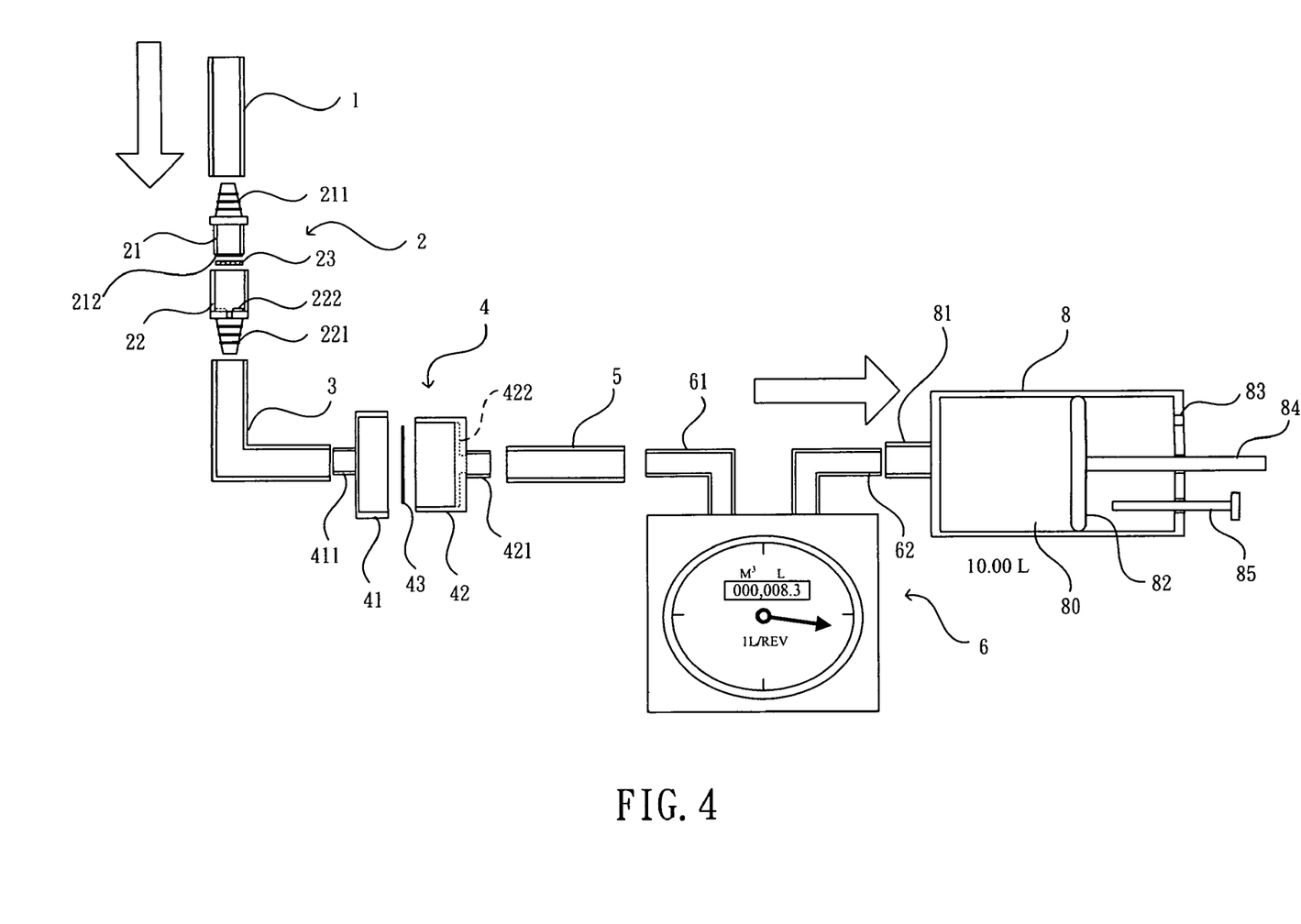
FIG. 4 is a schematic view of a quantitative sampler of pathogens in exhaled air according to a third embodiment of the present invention.

Referring now to FIG. 4, a quantitative sampler of pathogens in exhaled air according to a third embodiment of the present invention is illustrated and similar to the first embodiment, so that the third embodiment uses similar numerals and can be applied to the same quantitative analysis method. As shown, the quantitative sampler of pathogens in exhaled air according to the third embodiment further comprises a flow limiting unit 8 which is connected to the air outputting channel 62 of the air flow meter 6 for controlling a predetermined sampling volume of the exhaled air. In the third embodiment, the flow limiting unit 8 is a hollow cylinder which comprises an air inputting opening 81, a chamber 80, a piston 82, an air outputting opening 83, a push rod 84 and an adjusting rod 85. The air inputting opening 81 is communicated with the air outputting channel 62 of the air flow meter 6, while the chamber 80 is communicated with the air inputting opening 81 and the air outputting opening 83. The piston 82 is received in the chamber 80 and can be pushed by the exhaled air. The air inputting opening 81 and the air outputting opening 83 are formed on two different sides of the chamber 80 in relation to the piston 82. The push rod 84 has a first end connected to the piston 82 and a second end extended out of the hollow cylinder for manually pushing the piston 82. The adjusting rod 85 has a first end extended into the hollow cylinder and a second end extended out of the hollow cylinder. The adjusting rod 85 is preferably a thread rod, while a wall portion of the hollow cylinder has a thread hole (unlabeled) for screw-connecting to the adjusting rod 85.

When the quantitative sampler of the third embodiment of the present invention is used by a sampled individual, the push rod 84 is used to manually push the piston 82 until the piston 82 abuts against an inner wall of the chamber 80 close to the air inputting opening 81. Then, the adjusting rod 85 is used to adjust a maximum motion distance of the piston 82 in the chamber 80, so as to set a fixed maximum capacity of the chamber 80. In use, the exhaled air of the sampled individual passes through the air flow meter 6 and gradually flows into the flow limiting unit 8, wherein the exhaled air generates an air pressure to push the piston 82 in the chamber 80. Thus, the air originally received in the chamber 80 close to the air outputting opening 83 will be exhausted from the air outputting opening 83, so that the piston 82 can smoothly move. If the piston 82 move to abut against the first end of the adjusting rod 85, it means that total accumulated volume of the exhaled air reaches is equal to the fixed maximum capacity (such as 10 liters) of the flow limiting unit 8. Therefore, the piston 82 can not be further pushed, so that the sampled individual will be reminded that the quantitative exhaling operation is finished, so as to enhance the quantitative accuracy and the operational convenience. After the flow limiting unit 8 is used, the flow limiting unit 8 can be detached from the air outputting channel 62 of the air flow meter 6, and the push rod 84 can be manually pushed until the piston 82 abuts against the inner wall of the chamber 80 close to the air inputting opening 81 again for another sampled individual to repeatedly use. In addition, if wanting to change the setting of the predetermined sampling volume of the exhaled air, the present invention can select to adjust a new maximum motion distance of the piston 82 in the chamber 80 by the adjusting rod 85, so as to re-set a fixed maximum capacity (such as 5 liters) of the chamber 80.

The present invention has been described with a preferred embodiment thereof and it is understood that many changes and modifications to the described embodiment can be carried out without departing from the scope and the spirit of the invention that is intended to be limited only by the appended claims.

What is claimed is:

1. A quantitative sampler of pathogens in exhaled air for a general investigation of public health about the pathogens, comprising:
   an air inputting pipe for a sampled individual to blow exhaled air;
   a check valve unit having an air inputting end connected to the air inputting pipe, and an air outputting end;
   an aerosol filtering unit having a first opening connected to the air outputting end of the check valve unit, a second opening, and an aerosol filtering material disposed between the first opening and the second opening for collecting aerosol particles in the exhaled air; and
   an air flow meter having an air inputting channel connected to the second opening of the aerosol filtering unit, and an air outputting channel, wherein the air flow meter is used to measure if total accumulated volume of the exhaled air reaches a predetermined sampling volume;
   wherein the air outputting channel of the air flow meter is further connected to a flow limiting unit for controlling the sampling volume of the exhaled air;
   wherein the flow limiting unit is a hollow cylinder which comprises an air inputting opening, a chamber, a piston and an air outputting opening, wherein the air inputting opening is communicated with the air outputting channel of the air flow meter, the piston is received in the chamber and can be pushed by the exhaled air, and the air inputting opening and the air outputting opening are formed on two different sides of the chamber in relation to the piston;
   wherein the piston of the hollow cylinder is connected to a push rod which is extended out of the hollow cylinder for manually pushing the piston;
   wherein the hollow cylinder further comprises an adjusting rod which has a first end extended into the hollow cylinder and a second end extended out of the hollow cylinder for adjusting a maximum motion distance of the piston in the chamber, wherein the adjusting rod is a thread rod, and a wall portion of the hollow cylinder has a thread hole for screw-connecting to the adjusting rod; and
   wherein the push rod manually pushes the piston until the piston abuts against an inner wall of the chamber close to the air inputting opening, and the adjusting rod adjusts the maximum motion distance of the piston in the chamber, so as to set a fixed maximum capacity of the chamber for receiving the exhaled air; after the exhaled air of the sampled individual passes through the air flow meter and flows into the flow limiting unit, the exhaled air generates an air pressure to push the piston in the chamber, wherein air originally received in the chamber close to the air outputting opening is exhausted from the air outputting opening; once the piston moves to abut against the first end of the adjusting rod, a total accumulated volume of the exhaled air is equal to the fixed maximum capacity of the chamber, so that the piston can not be further pushed the exhaled air, and the sampled individual is thus reminded that the quantitative exhaling operation is finished; the flow limiting unit is detachable from the air outputting channel of the air flow meter, and the push rod can be manually pushed until the piston abuts against the inner wall of the chamber close to the air inputting opening again for another sampled individual to repeatedly use.

2. The quantitative sampler of pathogens in exhaled air of claim 1, wherein the air inputting pipe is further connected to a disposable blow pipe.

3. The quantitative sampler of pathogens in exhaled air of claim 1, wherein the aerosol filtering unit comprises at least two housings which commonly define an inner space for receiving the aerosol filtering material.

4. The quantitative sampler of pathogens in exhaled air of claim 1, wherein the pathogens in the exhaled air are virus, and the aerosol filtering material is a polytetrafluoroethylene filter.

5. The quantitative sampler of pathogens in exhaled air of claim 1, wherein the pathogens in the exhaled air are bacteria or fungi, and the aerosol filtering material is a polycarbonate filter.

6. The quantitative sampler of pathogens in exhaled air of claim 1, wherein the air flow meter is a dry-type air flow meter.

7. The quantitative sampler of pathogens in exhaled air of claim 1, wherein genetic substances of the pathogens are deoxyribonucleic acid or ribonucleic acid.

* * * * *